United States Patent [19]
Carbini et al.

[11] Patent Number: 5,311,868
[45] Date of Patent: May 17, 1994

[54] HOLDER FOR STEREOTACTIC FRAME

[75] Inventors: Carlos H. Carbini; Michael L. Goodman, both of Atlanta, Ga.

[73] Assignee: Peachtree Research & Development, Inc., Atlanta, Ga.

[21] Appl. No.: 957,715

[22] Filed: Oct. 7, 1992

[51] Int. Cl.⁵ .............................................. A61B 19/00
[52] U.S. Cl. .................................. 128/653.5; 606/130
[58] Field of Search ...................... 606/130; 128/653.1, 128/653.2, 653.5; 378/180

[56] References Cited

U.S. PATENT DOCUMENTS

| | | | |
|---|---|---|---|
| 4,592,352 | 6/1986 | Patil | 606/130 |
| 5,085,219 | 2/1992 | Ortendahl et al. | 128/653.5 |

Primary Examiner—Tamara L. Graysay
Attorney, Agent, or Firm—James B. Middleton

[57] ABSTRACT

A frame holder for a stereotactic frame holds the stereotactic frame in proper alignment with the head coil of an imaging unit so the reference markers on the stereotactic frame are properly aligned with the axis of the head coil. The frame holder has a base member that receives the base ring of the stereotactic frame so the frame holder and the stereotactic frame are locked together with proper alignment of the reference markers. A top member is spaced from the base member, and has a support block to carry the weight of the stereotactic frame. Posts fix the top member to the base member. The base and top member are sized and shaped to be snugly, slidably received within the opening in the head coil.

5 Claims, 2 Drawing Sheets

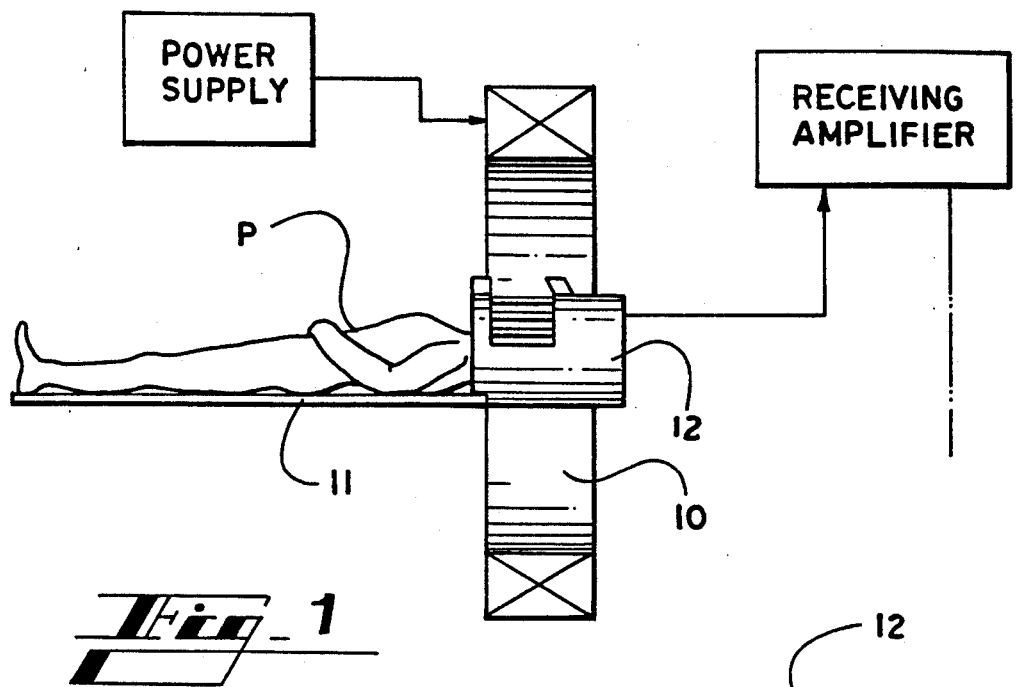
Fig_1
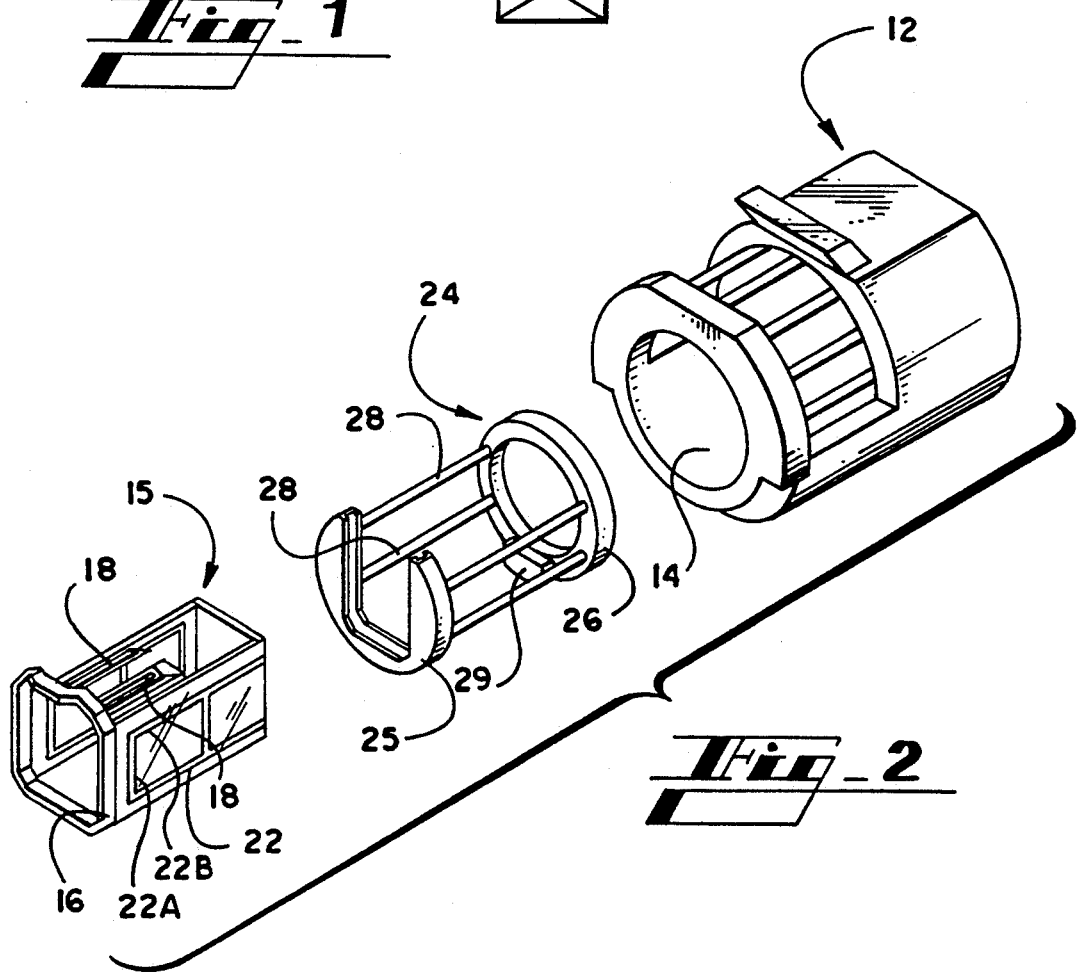
Fig_2

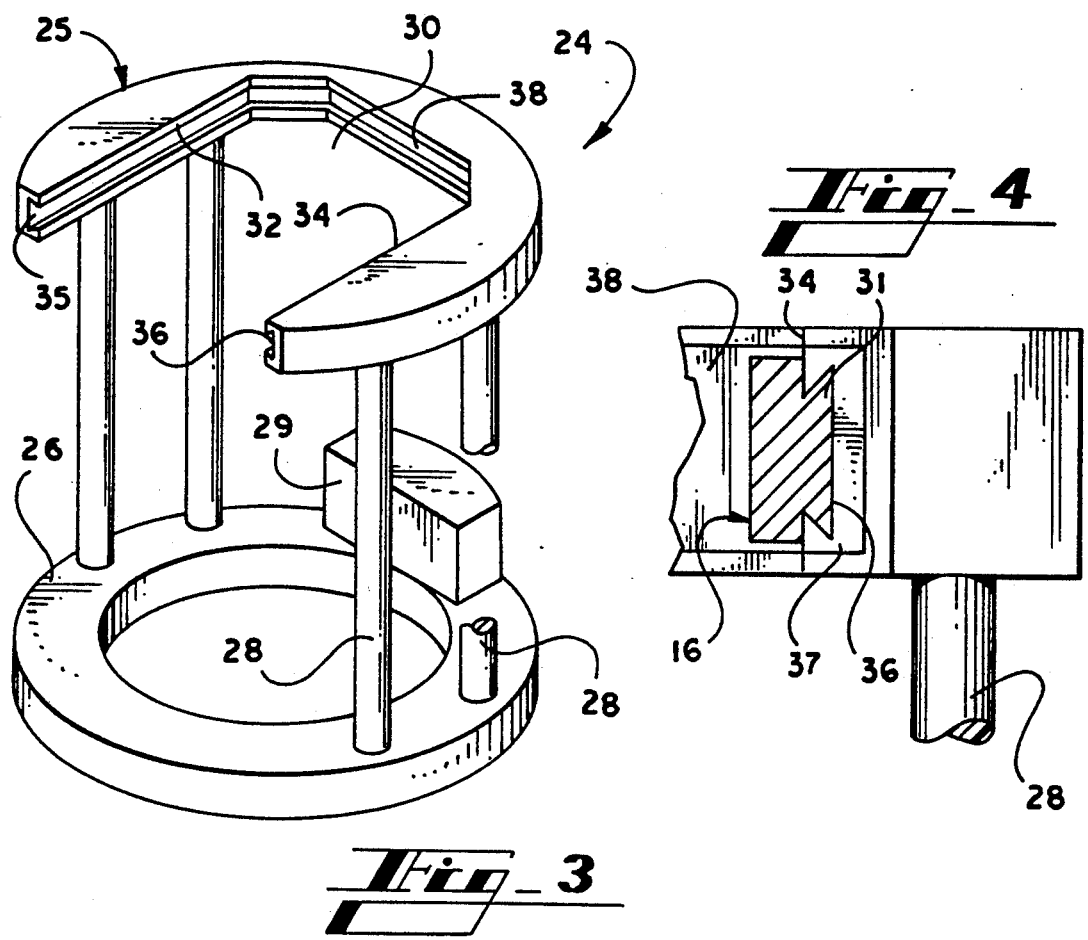
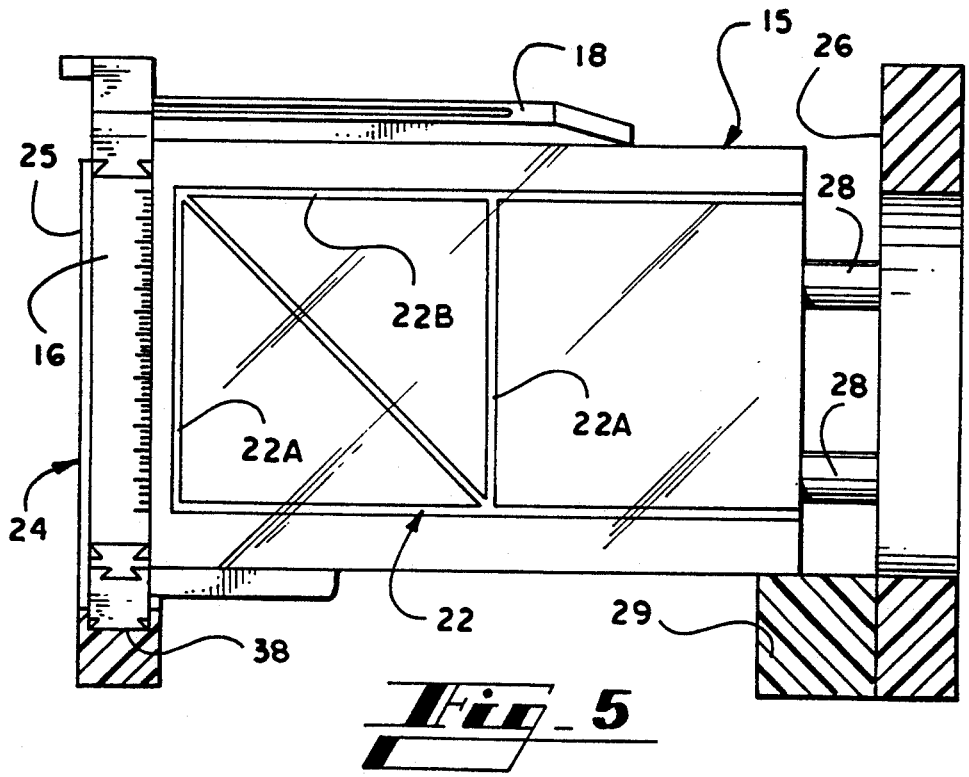

HOLDER FOR STEREOTACTIC FRAME

BACKGROUND OF THE INVENTION

1. Field of the Invention

This invention relates generally to stereotactic frames for use in stereotactic surgery, and is more particularly concerned with a frame holder for positioning a stereotactic frame with respect to an imaging system.

2. Description of the Prior Art

Stereotactic surgery requires that a particular point, for example in the head, be located by coordinates in three dimensional space. Currently, this is accomplished through the use of a stereotactic frame which has a coordinate system in conjunction therewith. With the patient in the stereotactic frame, images are made of the patient, using computer aided tomography (CAT), magnetic resonance imaging (MRI) or some comparable imaging system. The reference marks specifying the coordinate system of the stereotactic frame are visible on the images permitting calculation of coordinates of a chosen point.

Those skilled in the art will understand that the stereotactic frame defines a volume of three dimensional space, thereby allowing a positional description of any point in that defined volume to be made via the specified coordinate system. As a result, the surgeon must rely on the coordinate system to compute the precise location intended for surgery. It will therefore be understood that the attitude of the stereotactic frame with respect to the imaging device is important. A misalignment between the stereotactic frame and the imaging device will cause the coordinate reference markers on the stereotactic frame to be misaligned in the images. The mathematics of calculating the coordinates of a given point in the space defined by the stereotactic frame are significantly more complex without proper alignment of the stereotactic frame and the imaging system.

In making images of a patient's head using MRI, the head is placed within a "head coil" which is a transceiver for the radio-frequency (RF) signals of interest. The head coil defines a central opening for receiving the patient's head, and for receiving the head with a stereotactic frame thereon for stereotactic surgery. It is here that alignment is important. The stereotactic frame is preferably precisely aligned with the head coil in order to facilitate coordinate calculation.

The usual efforts at aligning a stereotactic frame with the head coil comprise attempting to prop up various portions of the frame with towels or the like. It will be understood that the material used must be carefully selected. Metals will redirect, or shield, the signals of interest, and numerous other materials will produce signals of their own. Ferrous metals cannot safely be placed in the room holding the MRI scanner due to the strength of the corresponding magnetic field and the risk of resulting movement. Thus, towels are commonly used in attempts to hold the frame in place. Since towels are deformable, they must be packed carefully. Even so, the frame frequently moves with respect to the head coil after imaging has begun. A shift in the frame may render calculation more difficult if the shift is before the actual scan, or may require a new scan if the shift is during the scan.

SUMMARY OF THE INVENTION

The present invention provides means for supporting a stereotactic frame with respect to an imaging device to assure proper alignment of the coordinate system in the images. The stereotactic frame is fixed to the patient; then, the stereotactic frame is inserted into the frame holder of the present invention. The frame holder of the present invention is then inserted into the imaging device, and the frame holder is so dimensioned that the frame holder, hence the stereotactic frame, is held in the desired attitude.

In one embodiment of the invention, the base ring of the stereotactic frame has dovetails along three sides thereof, and the frame holder includes means for receiving one or more of these dovetails for attachment of the stereotactic frame to the frame holder. A support block is provided for assuring proper alignment of the frame with the frame support.

Since the stereotactic frame is held to the frame holding device, alignment of the coordinate system is assured. One axis of the coordinate system is parallel to the base ring of the frame, and the frame is secured to the frame holder. Thus, the coordinate system will be properly aligned.

BRIEF DESCRIPTION OF THE DRAWING

These and other features and advantages of the present invention will become apparent from consideration of the following specification when taken in conjunction with the accompanying drawings in which:

FIG. 1 is a schematic illustration showing the use of magnetic resonance imaging utilizing a head coil;

FIG. 2 is an exploded perspective view showing the head coil illustrated in FIG. 1, and a stereotactic frame and a stereotactic frame holder made in accordance with the present invention;

FIG. 3 is an enlarged perspective view showing the frame holder illustrated in FIG. 2;

FIG. 4 is a fragmentary detail view showing the means for locking the frame to the frame holder; and, FIG. 5 is a longitudinal cross-sectional view of the frame holder shown in FIGS. 2 and 3, with a stereotactic frame therein.

DETAILED DESCRIPTION OF THE EMBODIMENT

Referring now more particularly to the drawings, and to that embodiment of the invention here presented by way of illustration, FIG. 1 shows the main coil 10 of a magnetic resonance imaging (MRI) device, and a platform 11 to receive the patient P. As here shown, the head of the patient P is within a head coil 12. Those skilled in the art will understand that the coil 10 is energized to produce a magnetic field. The magnetic field excites selected substances in the body of the patient, and molecules of the selected substance emit a signal that is detected, for example by the head coil 12. The signals are detected, and are stored with both the intensity of the signal and the particular angle from the receiver. The plurality of vectors is then assembled into an image.

FIG. 2 shows the head coil 12, and it can be seen that the head coil 12 defines a central cylindrical opening 14 for receiving the head of the patient to be imaged. FIG. 2 also illustrates a stereotactic frame 15 that will be fixed to the head of a patient in order to make images for use in stereotactic surgery. The stereotactic frame includes a base ring 16 having attaching posts 18 mounted thereon. The attaching posts 18 are fixed to the head of the patient, and can be moved with respect to the base ring 16 so the patient's head can be appropriately located within the frame 15.

The frame 15 allows attachment of right and left side reference plates, and front and top reference plates. These reference plates contain marker lines which are visible on the scan images and thereby define the coordinate system for use with the frame. It will be understood that stereotactic frames made by different manufacturers will have different coordinate systems, and different reference indicators or the like on the stereotactic frame or attachments. Thus, the particular frame here disclosed is by way of illustration only. In the frame 15 here illustrated, the lines 22 are hollow tubes defined in the reference plates. These tubes can be filled with an appropriate liquid and will appear as lines or dots on the image generated by the MRI device. It should be noted that the line 22A is parallel to the base ring 16, and the lines 22B are perpendicular to the line 22A and to the base ring 16.

With the above discussion in mind, it will be realized that the centerline of the frame 15 will preferably be coaxial with the centerline of the opening 14 in the head coil. More importantly, the base ring 16, and the lines 22A, should be precisely perpendicular to the long axis of the head coil. Such an arrangement will simplify calculations with the coordinate system for locating points of interest for surgery.

It is here that the prior art is deficient. The prior art provides that the surgeons and/or technicians doing the imaging must prop up the stereotactic frame 15 on towels, surgical drapes and the like in an effort to hold the frame in the preferred attitude. Even if one is successful in propping up the frame 15, there is no assurance that the frame will not shift just before, or during, the actual imaging.

The solution to the problem as provided by the present invention comprises a stereotactic frame holder generally designated at 24. The frame holder 24 is superior to the prior art in that the frame holder receives, and is locked to, the stereotactic frame 15; then, the frame holder is coaxially received by the head coil 12. The frame holder 24 is dimensioned so that the frame holder cannot move radially with respect to the head coil.

Looking at the frame holder 24 in more detail, there is a base member 25 which is designed, to receive the base ring 16 of the frame 15. The base member 25 is arranged so the frame 15 will be positioned within the frame holder 24 coaxially, and this arrangement will be discussed in more detail hereinafter.

The frame holder 24 includes a top member 26 axially aligned with the base member 25. The base member 25 and the top member 26 are held in their spatial relationship by a plurality of rods 28. In view of the weight of the stereotactic frame, and especially considering the forces exerted by the frame when a patient's head is within the frame, it is preferable not to rely solely on the base member 25 to support the frame 15. Thus, there is a support block 29 fixed to the top member 26, the block 29 being so placed as to bear against the upper portion of the frame 15. In the embodiment of the invention here presented, the opening 14 in the head coil 12 is cylindrical, so the top member 25 and the base member 25 of the frame holder 24 are circular in shape. Those skilled in the art will note that the shape and size of the top member 24 and the base member 25 may vary to suit the particular MRI scanner.

Looking next at FIG. 3 of the, drawings it can be more clearly seen that the base member 25 has a generally circular outer perimeter, with an opening 30 that is shaped to receive the octagonal base ring 16 through one edge of the octagon is omitted on the base member. Since the shape is to coincide with the shape of the base ring 16 of the stereotactic frame 15, those skilled in the art will understand that the shape of the opening 30 may vary to suit the particular stereotactic frame being used.

Further, the periphery of the opening 30 is designed to receive the base ring 16 of the stereotactic frame 15 in locking relationship. The frame 15 here illustrated includes dovetails 31 on three sides of the base ring 16, and the base member 25 of the frame holder 24 is arranged to cooperate with these dovetails. It will be understood that there are no dovetails on the short sides at the corners of the frame 15. The sides 32 and 34 of the opening 30 are formed with dovetail grooves 35 and 36 sized to receive the dovetails 31. The back of the opening 30 defines a groove 38 wide enough to receive the base ring 16 without the locking arrangement. As a result, the base ring 16 can be engaged with the dovetails 31 and grooves 35 and 36 interengaged. The frame 15 can then be slid into the frame holder until the rear of the frame 15 is stopped by the rear groove 38. At this point, the frame 15 will also engage the block 29.

One of the dovetail engagements is shown more clearly in FIG. 4 where the base ring 16 is shown fragmentarily simply to show the engagement. It can also be seen in FIG. 4 that one might manufacture the frame holder 24 in two or more pieces if desired. The base member 25 can be molded, machined, or otherwise formed, with a uniform, wide groove therein. A separate piece 37 can then be inserted in the sides 32 and 34 to create the dovetail grooves 35 and 36.

The multiple piece manufacture has the advantages both of simpler manufacture and of allowing different materials to be used. By way of example, one might use a good structural material for most of the frame holder 24, and use a good bearing material for the piece 37. Those skilled in the art will readily select appropriate materials for the specific design. Nevertheless, one successful embodiment of the invention has been made of "Delrin" acetyl (polyoxymethylene), which has both good strength and good bearing properties.

From the foregoing, it will be understood that, in the use of the present invention, a stereotactic frame such as the frame 15 will be fixed to the head of a patient P, then the frame 15 will be slid into the frame holder 24. The base ring 16 of the frame is locked to the frame holder so the axes of the coordinate system are parallel and perpendicular to the frame holder. The frame holder 24 is then coaxially received by the opening in the head coil 12. The frame, frame holder and coil are therefore held in the desired positions so the coordinate system is properly aligned with the imaging system for ease in calculations.

It will of course be understood by those skilled in the art that the embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

We claim:

1. In an imaging system including a transceiver, a stereotactic frame having a front and a rear received on the head of a patient to be imaged and reference markers on said stereotactic frame for use in a coordinate system for stereotactic surgery, said stereotactic frame being selectively receivable in said transceiver for imaging said patient, the combination therewith of a stereotactic frame holder for supporting said stereotactic frame with respect to said transceiver, said frame holder including means for attaching said stereotactic frame to said frame holder for preventing movement of said stereotactic frame with respect to said frame holder, said frame holder having a size and shape to move longitudinally of said transceiver while preventing lateral movement thereof, said transceiver defining an opening having a longitudinal axis, said opening being adapted to receive said stereotactic frame therein, said stereotactic frame including a base ring, said frame holder including a base member for receiving said base ring, and means for maintaining said base member perpendicular to said longitudinal axis of said transceiver, said means for maintaining said base member perpendicular to said longitudinal axis comprising a top member parallel to said base member and fixed with respect thereto, post means extending from said base member to said top member for fixing said top member to with respect to said base member, said base ring of said stereotactic frame including dovetails, said base member of said frame holder defining dovetail slots for receiving said dovetails for fixing said base ring of said stereotactic frame with respect to said member of said frame holder, and further including a block fixed to said top member of said frame holder, said block being located to engage the rear of said stereotactic frame when said stereotactic frame is received by said frame holder.

2. In an imaging system as claimed in claim 1, and wherein said opening in said transceiver is generally cylindrical, the further improvement wherein said base member and said top member of said frame holder are circular and have diameters slightly less than the diameter of said opening in said transceiver.

3. A frame holder for a stereotactic frame, wherein said stereotactic frame includes a base ring having means for supporting said stereotactic frame, and reference markers on said stereotactic frame for use with a coordinate system for stereotactic surgery, said frame holder including a base member, means on said base member for receiving said means for supporting said stereotactic frame and for aligning said reference markers with said base member of said frame holder, wherein said frame holder further includes a top member spaced from said base member, and connecting means for fixing said top member with respect to said base member.

4. A frame holder as claimed in claim 3, and further including a block carried by said top member, said block being located to assist in holding said stereotactic frame in alignment with said frame holder.

5. A frame holder as claimed in claim 3, wherein said means for supporting said stereotactic frame comprises dovetails on at least two sides of said stereotactic frame, and said means on said base member for receiving said means for supporting said stereotactic frame comprises dovetail slots defined by said base member, said dovetails slots being sized to slidably receive said dovetails.

* * * * *